United States Patent [19]

Shore et al.

[11] Patent Number: 4,515,728

[45] Date of Patent: May 7, 1985

[54] SYNTHESIS OF HETERONUCLEAR OSMIUM CARBONYL HYDRIDES UNDER GASEOUS HYDROGEN

[75] Inventors: Sheldon G. Shore, Columbus; Wen-Liang Hsu, Copley, both of Ohio

[73] Assignee: The Ohio State University Research Foundation, Columbus, Ohio

[21] Appl. No.: 504,479

[22] Filed: Jun. 15, 1983

Related U.S. Application Data

[63] Continuation-in-part of Ser. No. 322,447, Nov. 18, 1981, Pat. No. 4,389,347.

[51] Int. Cl.$^3$ .............................................. C07F 15/00
[52] U.S. Cl. ....................... 260/429 CY; 260/429 AR; 260/439 CY
[58] Field of Search ................. 260/429 CY, 429 AR, 260/439 CY

[56] References Cited

U.S. PATENT DOCUMENTS

| | | | |
|---|---|---|---|
| 2,985,504 | 5/1961 | Orchin | 423/417 |
| 3,006,940 | 10/1961 | Fischer et al. | 260/429 CY |
| 3,236,597 | 2/1966 | Knap | 423/417 |
| 3,505,034 | 4/1970 | L'Eplattenier et al. | 260/429 R |
| 3,597,461 | 8/1971 | L'Eplattenier et al. | 260/429 R |
| 4,282,197 | 8/1981 | Shore et al. | 423/417 |
| 4,349,521 | 9/1982 | Shore et al. | 423/417 |
| 4,349,522 | 9/1982 | Shore et al. | 423/417 |
| 4,389,347 | 6/1983 | Shore et al. | 260/429 CY |

OTHER PUBLICATIONS

Moss et al., J. Organometal Chem. 23 C23–C24 (1970).
Geoffroy et al., JACS 99 pp. 7565–7573 (1977).

*Primary Examiner*—Helen M. S. Sneed
*Attorney, Agent, or Firm*—Sidney W. Millard

[57] ABSTRACT

A process for producing a osmium heteronuclear metal carbonyl compound comprises establishing a reaction mixture comprising an electron deficient cobalt, nickel, iron, molybdenum or rhodium carbonyl, $H_2Os_3(CO)_{10}$ and a solvent in the presence of gaseous hydrogen and recovering the osmium heteronuclear metal carbonyl compound from the reaction mixture. Some of the cobalt, molybdenum and rhodium carbonyls produced are new. If the reaction with $Rh(\eta^5\text{---}C_5H_5)(CO)_2$ in conducted in benzene or toluene as solvent, the cyclopentadienyl liquid is replaced by a benzene or toluene ligand, thereby producing novel benzene- and toluene-substituted rhodium/osmium heteronuclear carbonyl hydrides.

27 Claims, No Drawings

SYNTHESIS OF HETERONUCLEAR OSMIUM CARBONYL HYDRIDES UNDER GASEOUS HYDROGEN

The government has rights in this invention pursuant to Grant CHE-79-18149 awarded by the National Science Foundation.

This application is a continuation-in-part of our co-pending application Ser. No. 322,447 filed Nov. 18, 1981 (now U.S. Pat. No. 4,389,347).

BACKGROUND OF THE INVENTION

In U.S. Pat. No. 4,349,522 which has one inventor (Sheldon G. Shore) in common with this application and which is assigned to the same Assignee as this application (the disclosure of the aforementioned U.S. Pat. No. 4,349,522 being incorporated herein by reference), the prior art relating to the reactions of $H_2Os_3(CO)_{10}$ is reviewed. This prior art indicates that $H_2Os_3(CO)_{10}$ normally reacts as a Lewis acid.

The aforementioned U.S. Pat. No. 4,349,522 demonstrates for the first time that $H_2Os_3(CO)_{10}$ also possesses apparent Lewis base character and discloses a process for making a tri-osmium heteronuclear metal carbonyl compound which comprises establishing a reaction mixture comprising an electron deficient cobalt, nickel or iron carbonyl or a cobalt, nickel or iron carbonyl anion, $H_2Os_3(CO)_{10}$, and a solvent which at least partially solubilizes at least one of the electron deficient carbonyl compound and the $H_2Os_3(CO)_{10}$, the $H_2Os_3(CO)_{10}$ reacting with the electron deficient carbonyl compound as a Lewis base, and recovering the tri-osmium heteronuclear metal carbonyl compound from the reaction mixture. Among the specific examples of this process described in detail in the aforementioned application are the reaction of $Co_2(CO)_8$ and $H_2Os_3(CO)_{10}$ to produce a major proportion of $HCoOs_3(CO)_{13}$ and a minor proportion of $H_3CoOs_3(CO)_{12}$, and the reaction of $[(\eta^5-C_5H_5)Ni(CO)]_2$ with $H_2Os_3(CO)_{10}$ to produce $H_3(\eta^5-C_5H_5)NiOs_3(CO)_9$. The yield of $H_3CoOs_3(CO)_{12}$ in the first of these two reactions is only about 5%, while the yield of $H_3(\eta^5-C_5H_5)NiOs_3(CO)_9$ in the second reaction is about 50%.

We have now discovered that, by carrying out the reaction described in the aforementioned application using the electron deficient carbonyl in the presence of gaseous hydrogen, the yields of certain of the tri-osmium nuclear metal carbonyl compounds produced can be markedly increased, and new carbonyls produced. In the case of the reactions described in the aforementioned application which produce a mixture of two products, the ratios between the two products can be shifted dramatically, so much so that in some cases what was formerly the minor product of the reaction becomes the only detectable product thereof. Furthermore we have also found that, by carrying out the reaction in the presence of hydrogen, carbonyls of metals other than cobalt, nickel or iron may be employed in the reaction.

SUMMARY OF THE INVENTION

Accordingly, the invention provides a first process for producing a tri-osmium heteronuclear metal carbonyl compound, which comprises establishing, in the presence of gaseous hydrogen, a reaction mixture comprising an electron deficient cobalt, nickel, iron, molybdenum or rhodium carbonyl, $H_2Os_3(CO)_{10}$ and a solvent which at least partially solubilizes at least one of the electron deficient carbonyl compound and the $H_2Os_3(CO)_{10}$, the reaction mixture being established in the substantial absence of molecular oxygen and water and recovering the tri-osmium heteronuclear metal carbonyl compound from the reaction mixture.

The invention also provides a second process for producing $H_4(\eta^5-C_5(CH_3)_5)-RhOs_3(CO)_9$, which comprises establishing, in the presence of gaseous hydrogen, a reaction mixture comprising $Rh(\eta^5-C_5(CH_3)_5)(CO)_2$, $H_2Os_3(CO)_{10}$ and a solvent which at least partially solubilizes one of $Rh(\eta^5-C_5(CH_3)_5)(CO)_2$ and $H_2Os_3(CO)_{10}$, this reaction mixture being established in the substantial absence of molecular oxygen and water, and recovering the $H_4(\eta^5-C_5(CH_3)_5)RhOs_3(CO)_9$ from the reaction mixture.

The invention also provides a third process for producing a rhodium tri-osmium carbonyl of the formula $H_3(\eta^6-\phi R_6)RhOs_3(CO)_9$, wherein $\phi R_6$ represents a benzene ring bearing six groups R, each of the groups R being independently hydrogen or a methyl group, the process comprising establishing, in the presence of gaseous hydrogen, a reaction mixture comprising $Rh(\eta^5-C_5H_5)(CO)_2$, $H_2Os_3(CO)_{10}$ and an aromatic solvent of the formula $\phi R_6$, the reaction mixture being established in the substantial absence of molecular oxygen and water, and recovering $H_3(\eta^6-\phi R_6)-RhOs_3(CO)_9$ from the reaction mixture.

It will be appreciated that the second and third processes of the invention defined above are actually specific examples of the first process of the invention.

Finally, the invention provides the novel tri-osmium heteronuclear carbonyls:

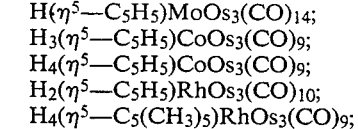

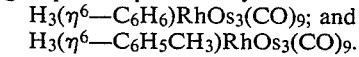

and the novel rhodium tri-osmium carbonyls of the formula $H_3(\eta^6-\phi R_6)RhOs_3(CO)_9$, wherein $\phi R_6$ represents a benzene ring bearing six groups R, each of said groups R being independently hydrogen or a methyl groups, and particularly:

$H_3(\eta^6-C_6H_6)RhOs_3(CO)_9$; and
$H_3(\eta^6-C_6H_5CH_3)RhOs_3(CO)_9$.

DETAILED DESCRIPTION OF THE INVENTION

In the instant processes, the contact between the gaseous hydrogen and the reactants may be commenced either before or after the reaction mixture itself is established. Thus, the reactants may be mixed together to form the reaction mixture under an atmosphere of gaseous hydrogen, or the reaction mixture may be first formed and only thereafter subjected to gaseous hydrogen. In practice, it is usually more convenient to form the reaction mixture and then to begin the passage of hydrogen therethrough; to ensure proper contact between the gaseous hydrogen and the liquid reaction mixture, preferably the hydrogen is bubbled through the reaction mixture.

The term "electron deficient metal carbonyl" as used herein includes not only those carbonyls which are truly electron deficient but also those carbonyls which are not electron deficient in the normal sense but which will disproportionate to yield an electron deficient disproportionation product, such as $Fe_2(CO)_9$, which disproportionates to yield $Fe(CO)_5$ and electron-deficient $Fe(CO)_4$.

The solvent used in the instant processes is desirably one which solubilizes both the electron deficient carbonyl and the $H_2Os_3(CO)_{10}$.

Preferred solvents for use in the instant processes are aromatic solvents, ether solvents and chlorohyrocarbon solvents, the exact choice of solvents depending of course on the particular electron deficient carbonyl compound being used. Preferably the molar ratio of the electron deficient carbonyl compound to the $H_2Os_3(CO)_{10}$ is at least about stoichiometric. The electron deficient carbonyl compound may, if desired, be generated in situ in the reaction mixture for reaction with the $H_2Os_3(CO)_{10}$.

Many of the tri-osmium heteronuclear complexes produced by the instant processes are sensitive to molecular oxygen and/or water. Accordingly, the reaction mixture should be established in the substantial absence of molecular oxygen and water, usually under an inert gas blanket.

Examples of reactions which may be conducted by the instant processes are as follows:

| | Electron deficient carbonyl compound | Heteronuclear tri-osmium product(s) |
|---|---|---|
| A | $Co_2(CO)_8$ | $H_3CoOs_3(CO)_{12}$. |
| B | $[(\eta^5-C_5H_5)Ni(CO)]_2$ | $H_3(\eta^5-C_5H_5)NiOs_3(CO)_9$** |
| C | $[(\eta^5-C_5H_5)Mo(CO)_3]_2$ | $H(\eta^5-C_5H_5)MoOs_3(CO)_{12}$ |
| | | $H(\eta^5-C_5H_5)MoOs_3(CO)_{14}$* |
| | | $H_3(\eta^5-C_5H_5)MoOs_3(CO)_{11}$ |
| D | $(\eta^5-C_5H_5)Co(CO)_2$ | $H_2(\eta^5-C_5H_5)CoOs_3(CO)_{10}$** |
| | | $H_3(\eta^5-C_5H_5)CoOs_3(CO)_9$* |
| | | $H_4(\eta^5-C_5H_5)CoOs_3(CO)_9$* |
| E(i) | $Rh(\eta^5-C_5H_5)(CO)_2$ (heptane solvent) | $H_2(\eta^5-C_5H_5)RhOs_3(CO)_{10}$* |
| E(ii) | $Rh(\eta^5-C_5H_5)(CO)_2$ (benzene solvent) | $H_2(\eta^5-C_5H_5)RhOs_3(CO)_{10}$* |
| | | $H_3(\eta^6-C_6H_6)RhOs_3(CO)_9$* |
| E(iii) | $Rh(\eta^5-C_5H_5)(CO)_2$ (toluene solvent) | $H_2(\eta^5-C_5H_5)RhOs_3(CO)_{10}$* |
| | | $H_3(\eta^6-C_6H_5CH_3)RhOs_3(CO)_9$* |
| F | $Rh(\eta^5-C_5(CH_3)_5)CO_2$ | $H_4(\eta^5-C_5(CH_3)_5)RhOs_3(CO)_9$* |

The two compounds in the above table marked with a double asterisk (**) are claimed in the aforementioned U.S. Pat. No. 4,349,522. The compounds marked with a single asterisk (*) are novel and this invention extends to these novel compounds per se.

Preferred conditions for each of the specific reactions tabulated above will now be discussed, the reactions being identified by the electron deficient starting material:

A $Co_2(CO)_8$

The solvent used in the reaction mixture is conveniently a chlorohydrocarbon, preferably methylene chloride. It is preferred to use at least one mole of $Co_2(CO)_8$ per mole of $H_2Os_3(CO)_{10}$ though more of the cobalt compound may be used if desired. The reaction mixture is desirably maintained at a temperature not above about room temperature (room temperature being defined for present purposes as 25° C.), room temperature being the preferred temperature for carrying out the reaction. The reaction mixture should desirably be established in the substantial absence of molecular oxygen and water.

After completion of the reaction, a substantial amount of $Co_4(CO)_{12}$ is present in the reaction mixture. To separate this by-product from the desired $H_3CoOs_3(CO)_{12}$, the reaction mixture is preferably chromatographed on silica gel using a hexane/benzene liquid phase.

B $[(\eta^5-C_5H_5)Ni(CO)]_2$

The solvent used in the reaction mixture is conveniently an aromatic solvent, preferably toluene. It is preferred to use at least one mole of $[(\eta^5-C_5H_5)Ni(CO)]_2$ per mole of $H_2Os_3(CO)_{10}$, though more of the nickel compound may be used if desired. The reaction mixture is desirably maintained at a temperature in the range of about 80° to about 120° C., and preferably at about 90° C.

As disclosed in the aforementioned copending application Ser. No. 06/275,693, when the reaction of $[(\eta^5-C_5H_5)Ni(CO)]_2$ with $H_2Os_3(CO)_{10}$ is carried out in the absence of hydrogen, the reaction produces not only $H_3(\eta^5-C_5H_5)NiOs_3(CO)_9$ but also a minor but substantial proportion of a by-product which displays no hydride resonances in its proton nuclear magnetic resonance spectrum. Carrying out the reaction in the presence of hydrogen increases the yield of $H_3(\eta^5-C_5H_5)NiOs_3(CO)_9$ to about 93% based upon the $H_2Os_3(CO)_{10}$ used. No substantial amount of the non-hydride by-product is formed, so that purification of the product is simplified.

The reaction is preferably carried out in the substantial absence of molecular oxygen and water.

C $[(\eta^5-C_5H_5)Mo(CO)_3]_2$

The solvent used in the reaction mixture is conveniently an aromatic solvent, preferably toluene. It is preferred to use at least one mole of $[(\eta^5-C_5H_5)Mo(CO)_3]_2$ per mole of of $H_2Os_3(CO)_{10}$, and indeed it is preferred to use the two reactants in substantially equimolar quantities. The reaction mixture is desirably maintained at a temperature in the range of about 80° to about 120° C., and preferably at about 90° C. The reaction mixture should desirably be established in the substantial absence of molecular oxygen and water.

As noted above, the reaction produces three separate products, namely $H(\eta^5-C_5H_5)MoOs_3(CO)_{12}$, $H(\eta^5-C_5H_5)MoOs_3(CO)_{14}$ and $H_3(\eta^5-C_5H_5)MoOs_3(CO)_{11}$. Separation of the products is conveniently effected by chromatography on silica gel, a convenient eluant being a 1:4 v/v benzene/hexane mixture.

D $(\eta^5-C_5H_5)Co(CO)_2$

The solvent used in the reaction mixture is conveniently an aromatic solvent, preferably toluene. It is preferred to use more than one mole of $(\eta^5-C_5H_5)Co(CO)_2$ per mole of $H_2Os_3(CO)_{10}$, and indeed in view of the relative cost of the two reactants, it is convenient to use approximately five moles of the cobalt compound per mole of the osmium compound. The reaction mixture is desirably maintained to a temperature in the range of about 80° to about 120° C., and preferably at about 90° C. The reaction mixture desirably is established in the substantial absence of molecular oxygen and water.

Separation of the three products of the reaction may conveniently be separated by chromatography under the same conditions described above with respect to reaction C.

E(i), (ii), and (iii), $(\eta^5-C_5H_5)Rh(CO)_2$

This reaction differs from those previously described in that the nature of the products produced varies with the solvent employed. If the reaction is carried out in an aliphatic hydrocarbon solvent, for example heptane, the reaction proceeds in a manner somewhat analogous to reaction D above, but the only identifiable product is $H_2(\eta^5-C_5H_5)RhOs_3(CO)_{10}$. In this case, it is preferred to use more than one mole of $Rh(\eta^5-C_5H_5)(CO)_2$ per mole of $H_2Os_3(CO)_{10}$, and indeed preferably about 5 moles of the rhodium compound are used per mole of the osmium compound. The reaction mixture is desirably maintained at a temperature in the range of about 80° to about 120° C., and preferably at about 90° C. In the substantial absence of molecular oxygen and water. Purification of the product may be effected by chromatography in substantially the same manner as described for reaction C.

If, however, this reaction is conducted in an aromatic solvent which is a potential hexahapto ligand, and in particular using as the solvent benzene or a methyl-substituted benzene such as toluene, there is produced, in addition to the $H_2(\eta^5-C_5H_5)RhOs_3(CO)_{10}$ already mentioned, a compound of the formula $H_3(\eta^6-\phi R_6)RhOs_3(CO)_9$, wherein $\phi R_6$ represents a benzene ring bearing 6 groups R, each of these groups R being independently hydrogen or a methyl group. In other words, part of the product is a rhodium tri-osmium carbonyl produced by displacement of the cyclopentadienyl ligand in the starting material with the hexahapto ligand solvent. To the best of our knowledge, this displacement of a cyclopentadienyl ligand by a benzene or benzene-derived ligand is unprecedented in this field. Thus, if benzene is used, in addition to the $H_2(\eta^5-C_5H_5)RhOs_3(CO)_{10}$ reaction using heptane as solvent, one obtains $H_3(\eta^6-C_6H_6)RhOs_3(CO)_9$, and if toluene is employed as the solvent $H_3(\eta^6-C_6H_5CH_3)RhOs_3(CO)_9$. When conducting the reaction using benzene or toluene as the solvent, it is preferred to use more than one mole of $Rh(\eta^5-C_5H_5)(CO_2)$ per mole of $H_2Os_3(CO)_{10}$ and indeed preferably about 2 moles of the rhodium compound are used per mole of the osmium compound. The remaining reaction conditions are the same as for conducting this reaction in heptane, and the products of the reaction are conveniently separated by chromatography in substantially the same manner as described for the products of reaction C above.

F($Rh(\eta^5-C_5(CH_3)_5)(CO)_2$

The solvent used in the reaction mixture may be either an aliphatic or an aromatic solvent, such as heptane, toluene or benzene, since the reaction proceeds in the same manner in both aliphatic and aromatic hydrocarbons; unlike the corresponding reaction with the corresponding unsubstituted cyclopentdienyl compound, there is no evidence for displacement of the pentamethycyclopentadienyl ligand when the reaction is conducted in an aromatic solvent. The preferred conditions for this reaction are the same as those for those using the unsubstituted cyclopentadienyl compound described in reaction E above.

The instant process is not restricted to the specific reactions A-F described in detail above, but may be used for insertion of other transition metals into the triosmium framework. Such other pathways would involve the reaction of $H_2Os_3-(CO)_{10}$ with an electron deficient (electrophilic) metal complex or intermediate complex. Such a system relies on the apparent Lewis base property or nucleophilicity of the tri-osmium cluster for synthesizing new heteronuclear metal clusters. While any transition metal could form the electron deficient metal complex, cobalt, nickel, molybdenum and rhodium are preferred as the metal of the electron deficient complex. Similarly, such electron deficient species need not be carbonyl complexes, but carbonyl complexes are preferred. Suitable solvents would be those solvents disclosed herein which solubilize at least one of the electron deficient metal complex and the tri-osmium reactant. It must be recognized that for each system the reaction conditions (e.g. temperature, molar ratio of reactants, tolerance of water, tolerance of molecular oxygen, etc.) may vary somewhat, but determination of such reaction conditions will be routine based on the disclosure herein contained.

In view of the proven ability of $H_2Os_3(CO)_{10}$ and $Os_3(CO)_{12}$ to catalyze olefin isomerizations, the mixed-metal clusters produced by the instant process are expected to have potential catalytic activity. Such clusters may perhaps be chemically attached to supports to provide a heterogeneous catalyst system analagous to the systems described by Pierantozzi et al., JACS, 101;18, 5436-5438 (1979). Moreover, such supported mixed-metal cluster compounds may have further utility by their reduction on the support to produce new bi-metallic cluster candidates having unique surface properties. Further information on such surface properties can be found in McVicker and Vannice, "The Preparation, Characterization and Use of Supported Potassium-group VIII Metal Complexes as Catalysts for CO Hydrogenation", Exxon Research and Engineering Company, Corporate Pioneering Research Laboratories, Linden, N.J. (1979). Further data on transition metal carbonyl cluster catalysts is disclosed in Basset and Smith, Abstracts of Invited Talks, XIX, International Conference on Pure and Applied Chemistry, Prague, Czechoslovakia, pages 161-164 (1978). For a good discussion on cluster catalysis, reference is made to J. J. Bassett and R. Ugo, Aspects of Homogeneous Catalysis, Chapter 2, Vol. 3, D. Ridel, Dordrecht, Holland, (1977). In particular, the heteronuclear tri-osmium complexes produced by the instant method are believed to be useful as Fischer-Tropsch catalysts.

Examples of the instant process will now be given, by way of illustration only.

EXAMPLE 1

Preparation of $H_3CoOs_3(CO)_{12}$ from $Co_2(CO)_8$ 60 mg. of $H_2Os_3(CO)_{10}$ (0.07 mmol.) and 26 mg. of $Co_2(CO)_8$ (0.07 mmol.) were placed in a 50 ml. three-necked flask equipped with a condenser. Approximately 20 ml. of anhydrous methylene chloride (distilled from phosphorous pentoxide) were then condensed into the flask at −78° C. After degassing by two freeze-pump-thaw cycles, the resultant reaction mixture was warmed to room temperature and magnetically stirred at this temperature for 24 hours while gaseous hydrogen was slowly bubbled through the solution. After the 24 hours stirring, a spot test by thin-layer chromatography indicated that complete consumption of the $H_2Os_3(CO)_{10}$.

The methylene chloride and a small remaining amount of $Co_2(CO)_8$ were removed from the reaction mixture under vacuum to leave a brownish yellow residue. This residue was dissolved in a 1:1 v/v benzene/hexane mixture and chromatographed on a silica gel column. Elution with hexane gave a dark brown band, identified by infrared spectroscopy as consisting of $Co_4(CO)_{12}$ and a small amount of $H_2Os_3(CO)_{12}$. A yellow band that remained at the top of the column was eluted with a 1:1 v/v benzene/hexane mixture and the solvent was removed in a rotary evaporator to leave 41 mg. of the orange-yellow product, $H_3CoOs_3(CO)_{12}$ (60% yield based on the $H_2Os_3(CO)_{10}$ starting material, identical to that produced as a by-product in the process described in Example 5 of the aforementioned copending application Ser No. 06/275,693. The infrared spectrum in cyclohexane showed carbonyl bands at 2078(vs), 2062(m,sh), 2048(w), 2030(vs), 2025(vs), 2005(m), 1998(w,sh), 1980(vw) cm$^{-1}$. The known spectrum from the literature is 2076(vs), 2066(ms), 2049(w), 2030(vs), 2025(vs), 2012(w), 2005(s), 2000(sh) and 1982(w) cm$^{-1}$. The proton magnetic resonance spectrum in deuterochloroform showed a single peak at $\delta = -19.03$ ppm., the literature value of this compound in methylene chloride being $\delta = -19.1$ ppm.

EXAMPLE 2

Preparation of $H_3(\eta^5-C_5H_5)NiOs_3(CO)_9$ from $[(\eta^5-C_5H_5)Ni(CO)]_2$ 60 mg. of $H_2Os_3(CO)_{10}$ (0.07 mmol.) and 21 mg. of $[(\eta^5-C_5H_5)Ni(CO)]_2$ (0.07 mmol.) were placed in a 50 ml. three-necked flask equipped with a condensor. Approximately 20 ml. of anhydrous toluene was condensed at $-78°$ C. into the flask. After degassing by two freeze-pump-thaw cycles, the resultant reaction mixture was warmed to 90° C. and magnetically stirred at this temperature for 10 hours while gaseous hydrogen was slowly bubbled through the solution. At the end of this 10 hours stirring, the infrared spectrum of a sample of the reaction mixture indicated the complete consumption of the $H_2Os_3(CO)_{10}$. $H_3(\eta^5-C_5H_5)NiOs_3(CO)_9$ was the only species other than the solvent observable in the infrared spectrum. The toluene was removed from the reaction mixture in a rotary evaporator under reduced pressure to leave a purple residue which was purified by chromatography on a silica gel column using a 1:4 v/v benzene/hexane mixture as eluant. After removal of the benzene/hexane solvent, the resultant residue was recrystalized from methylene chloride/hexane to give 62 mg. of dark purple, crystalline $H_3(\eta^5-C_5H_5)NiOs_3(CO)_9$ (93% based on $H_2Os_3(CO)_{10}$), identical to the product produced in Example 6 of the aforementioned copending application Ser. No. 06/275693.

EXAMPLE 3

Preparation of $H(\eta^5-C_5H_5)MoOs_3(CO)_{12}$, $H(\eta^5-C_5H_5)MoOs_3(CO)_{14}$, and $H_3(\eta^5-C_5H_5)MoOs_3(CO)_{11}$ from $[(\eta^5-C_5H_5)Mo(CO)_3]_2$ 150 mg. of $H_2Os_3(CO)_{10}$ (0.176 mmol.) and 87 mg. of $[(\eta^5-C_5H_5)Mo(CO)_3]_2$ (0.176 mmol.) were placed in a 50 ml. three-necked flask equipped with a condenser and maintained under a nitrogen atmosphere. Approximately 20 ml. of freshly distilled and degassed toluene was added to the flask. Pre-purified hydrogen gas was slowly bubbled through the reaction mixture, which was heated to 90° C. and maintained at this temperature, under stirring, for six days. At the end of this six-day reaction period, a spot test of the reaction mixture by thin layer chromatography indicated complete consumption of the $H_2Os_3(CO)_{10}$. Accordingly, the reaction mixture was cooled to room temperature and the toluene removed under reduced pressure on a rotary evaporator to leave a brownish residue.

This residue was dissolved in 5 ml. of methylene chloride and subjected to thin layer chromatography on silica gel (grade EM-60-F-254, the silica gel layer being 0.5 mm. in thickness) using a 1:4 v/v benzene/hexane mixture as the eluant. This chromatographic separation produced four bands; in order of decreasing $R_f$ values, the bands were yellow, pink, orange and reddish-brown. All four bands were separately scraped off the chromatography plate and eluted from the silica gel with methylene chloride. The methylene chloride was removed in a rotary evaporator and, except for the pink residue (which was found to be unchanged $[(\eta^5-C_5H_5)Mo(CO)_3]_2$), the separated residues were weighed and their high-resolution mass spectra, infrared spectra and proton magnetic resonance spectra recorded.

The yellow band yielded 18 mg. (6.4% based on the $H_2Os_3(CO)_{10}$) of $H(\eta^5-C_5H_5)MoOs_3(CO)_{14}$. The mass spectrum of this compound showed a parent peak at $m/e = 1132$, consistant with $^1H_6{}^{12}C_{19}{}^{16}O_{14}{}^{98}Mo{}^{192}Os_3$. The infrared spectrum in cyclohexane showed bands at 2072(s), 2058(vs), 2048(s), 2028(m), 2018(s), 2008(m) and 1990(w,sh) cm$^{-1}$. The proton magnetic resonance spectrum in deuterochloroform showed a singlet at $\delta = 5.28$ (5H), and a singlet at $\delta = -20.51$ (1H) ppm.

The orange band produced 20 mg. (11% based on the $H_2Os_3(CO)_{10}$ of $H_3(\eta^5-C_5H_5)MoOs_3(CO)_{11}$. The mass spectrum of this compound showed a parent peak at $m/e = 1050$, consistent with $^1H_8{}^{12}C_{16}{}^{16}O_{11}{}^{98}Mo{}^{192}Os_3$. The infrared spectrum in cyclohexane showed peaks at 2082(m), 2052(s), 2046(vs), 2008(m), 1999(m), 1962(w) and 1953(s) cm$^{-1}$. The proton magnetic resonance spectrum in deuterochloroform showed singlets at $\delta = 5.26$ (5H) and $-19.57$ (3H).

Finally the reddish-brown band produced 12 mg. (9% based on the $H_2Os_3(CO)_{10}$) of $H(\eta^5-C_5H_5)MoOs_3(CO)_{12}$. The infrared spectrum of this compound in hexane showed peaks at 2079(vw), 2068(w), 2042(vs), 2023(s), 1995(s), 1986(m), 1960(vw), 1945(vw) and 1842(w) cm$^{-1}$. The proton magnetic resonance spectrum in deuterochloroform showed singlets at $\delta = 5.56$ (5H) and $-18.16$ (1H) ppm at room temperature.

Both $H_3(\eta^5-C_5H_5)MoOs_3(CO)_{11}$ and $H(\eta^5-C_5H_5)MoOs_3(CO)_{12}$ have been previously reported in the literature, but no spectral data have been given. See M. R. Churchill, F. J. Hollander, J. R. Shapley and D. S. Foose, J.Chem. Comm (1978), page 534.

EXAMPLE 4

Preparation of $H_3(\eta^5-C_5H_5)CoOs_3(CO)_9$, $H_4(\eta^5-C_5H_5)CoOs_3(CO)_9$ and $H_2(\eta^5-C_5H_5)CoOs_3(CO)_{10}$ from $(\eta^5-C_5H_5)Co(CO)_2$ 150 mg. of $H_2Os_3(CO)_{10}$ (0.176 mmol.) and 167 mg. of $(\eta^5-C_5H_5)Co(CO)_2$ (0.88 mmol.) were placed in a 50 ml. three-necked flask equipped with a condenser and maintained under a nitrogen atmosphere. Approximately 20 ml. of freshly distilled and degassed toluene was added to the flask. Pre-purified hydrogen gas was slowly bubbled through the resultant mixture, which was heated to 90° C. and kept at this temperature for 53 hours with stirring. At the end of this reaction period, the infrared spectrum of a sample of the reaction mixture indicated complete consumption of the $H_2Os_3(CO)_{10}$. Accordingly, the reaction mixture was cooled to room temperature and the toluene and the unconsumed cobalt carbonyl were removed under vacuum to leave a dark brown residue, which was dissolved in about 5 ml. of methylene chloride and subjected to thin layer chromatography using the same technique as in Example 3 except that preparative plates having a 2.0 mm. layer of silica gel were employed. The chromatogram showed three distinct bands, these being, in descending order of $R_f$ values, purple, dark green and green. The three bands were separately scraped off the plate, eluted with methylene chloride and the solvent removed in exactly the same manner as in Example 3.

The green band having the smallest $R_f$ produced 7.2 mg. (4% based on the $H_2Os_3(CO)_{10}$) of $H_2(\eta^5-C_5H_5)CoOs_3(CO)_{10}$ identical to the product produced in Example 3 of the aforementioned application Ser. No. 06/275,693.

The purple band produced 55 mg. (33% based on the $H_2Os_3(CO)_{10}$) of $H_3(\eta^5-C_5H_5)CoOs_3(CO)_9$. A high-resolution mass spectrum of this compound showed a parent peak at m/e=954.8369, consistent with $^{12}C_{14}{}^1H_8O_9{}^{59}Co{}^{192}Os_3$ (the theoretical molecular weight is 954.8336). The infrared spectrum of this compound in hexane showed peaks at 2082(w), 2060(s), 2008(vs), 1990(m) and 1955(vw) cm$^{-1}$.

The dark green band produced 53 mg. (32% based on the $H_2Os_3(CO)_{10}$) of $H_4(\eta^5-C_5H_5)CoOs_3(CO)_9$. The high-resolution mass spectrum of this compound showed a parent peak at m/e=955.8387, consistent with $^{12}C_{14}{}^1H_9{}^{16}O_9{}^{59}Co{}^{192}Os_3$ (the theoretical molecular weight is 955.8415). The infrared spectrum of this compound in hexane showed peaks at 2082(m), 2060(s), 2050(s), 2010(s), 1995(s,sh), 1992(s), 1977(m) and 1952(vw) cm$^{-1}$. At room temperature the proton magnetic resonance spectrum of this compound in deuterochloroform showed singlets at $\delta = 5.22$ (5H) and $-19.30$ (4H) ppm. At $-60°$ C., the singlet at $\delta = 5.22$ was unchanged, but the singlet at $\delta = -19.30$ was resolved into two singlets at $-18.26$ (2H) and 20.27 (2H) ppm. The $^{13}C$ proton-coupled nuclear magnetic resonance spectrum in methylene chloride at room temperature showed peaks at 79.7 ($J_{C-H} = 180.4$ Hz, attributed to cyclopentadibenyl carbons), 171.2 (attributed to equatorial terminal carbonyls) and 176.8 (attributed to axial terminal carbonyls) ppm.

Based upon the foregoing spectral data, it is believed (though the invention is in no way limited by this belief) that the structure of $H_3(\eta^5-C_5H_5)CoOs_3(CO)_9$ is that of a tetrahedron of metal atoms, the cyclopentadienyl ligand being coordinated with the cobalt atom, three carbonyls being coordinated with each of the osmium atoms, and each of the Os—Os edges of the tetrahedron being bridged by a single hydrogen atom. In the compound $H_4(\eta^5-C_5H_5)CoOs_3(CO)_9$, the disposition of the cobalt, osmiums, carbonyls and cyclopentadienyl is similar but only two of the Os—Os edges are bridged by hydrogen atoms, the other two hydrogen atoms bridging the Os—Co edges of that face of the tetrahedron whose Os—Os edge is not bridged by a hydrogen atom.

A further experiment showed that the $H_3(\eta^5-C_5H_5)CoOs_3(CO)_9$ produced in the above experiment could be substantially completely converted to $H_4(\eta^5-C_5H_5)CoOs_3(CO)_9$ by slowly bubbling pre-purified hydrogen through a solution of the starting material in toluene at a temperature of 90° C. for 48 hours.

EXAMPLE 5

Preparation of $H_2(\eta^5-C_5H_5)RhOs_3(CO)_{10}$ and $H_3(\eta^6-C_6H_5CH_3)RhOs_3(CO)_9$ from $Rh(\eta^5-C_5H_5)(CO)_2$ 150 mg. of $H_2Os_3(CO)_{10}$ (0.176 mmol.) and 196 mg. of $Rh(\eta^5-C_5H_5)(CO)_2$ (0.88 mmol.) were placed in a 50 ml. three-necked flask equipped with a condenser and maintained under a nitrogen atmosphere. Approximately 20 ml. of freshly distilled and degassed toluene was added to the flask. Pre-purified hydrogen gas was slowly bubbled through the resultant reaction mixture which was heated to 90° C. and maintained at this temperature for 72 hours with stirring. At the end of this reaction period, the infrared spectrum of a sample of the reaction mixture indicated the complete consumption of the $H_2Os_3(CO)_{10}$. Accordingly, the reaction mixture was cooled to room temperature and the toluene removed under vacuum to leave a reddish-brown oil, which was redissolved in 5 ml. of methylene chloride and subjected to thin-layer chromatography under the same conditions as in Example 4. The resultant chromatogram showed three bands, these being, in order of decreasing $R_f$ values, orange, greenish-brown and brown. These three bands were separately scraped off the plate, eluted with methylene chloride and the solvent removed by rotary evaporation. The brown band produced 14 mg. of an unidentified brown solid, the infrared spectrum of which is hexane showed peaks at 2080(w), 2065(s), 2045(w,sh), 2039(vs), 2006(vs), 1995(vs), 1962(m), 1932(vw), 1830(vw) and 1808(m) cm$^{-1}$.

The orange band produced 45 mg. (26% based on the $H_2Os_3(CO)_{10}$) of an orange-red compound. The infrared spectrum of this compound in hexane showed peaks at 2070(w), 2046(s), 1999(vs) 1984(m) and 1950(vw) cm$^{-1}$. This infrared spectrum is very similar to that of the isostructural clusters $H_3(\eta^5-C_5H_5)MOs_3(CO)_9$, wherein M is cobalt or nickel. The proton NMR spectrum in hexadeuteroacetone show a multiple at $5 = 6.35$ ppm. (5H, attributable to phenyl protons), a singlet at $5 = 2.33$ ppm (3H) and a singlet at $5 = -17.2$ ppm (3H, attributable to bridging hydrides). Accordingly, in an effort to resolve the structure of this compound, it was subjected to a full, three-dimensional X-ray diffraction study using a Syntex P2$_1$ automated four-circle diffractometer and the structure solved by direct, MULTAN methods, difference-Fourier synthesis and full-matrix, least-squares refinement, the crystallographic computations being carried out on a NOVA 1200 computer using the syntex XTL structure solving package, as modified by the State University of New York at Buffalo.

The results of this crystalographic analysis showed the compound to have the formula $H_3(\eta^6-C_6H_5CH_3)RhOs_3(CO)_9$. The space group was B2/m (#12) with cell parameters a=14.178A, b=14.683A, c=10.205A and $\beta$=92.89°, giving a cell volume of 2121.6A$^3$ and a calculated specific gravity of 3.20, assuming a molecular weight of 1020.78 and 4 molecules per cell in special positions; x, y, o; $\bar{x}$, $\bar{y}$, o. Final discrepancy indices were $R_F$=3.9% and $R_{wF}$=4.0% for all 1964 independent reflections having $4° < 2\theta < 50°$ with MoK$\alpha$ radiation, and $R_F$=3.2° and $R_{wF}$=3.8% for those 1726 reflections with $|F_O| > 3\sigma(|F_O|)$. The structure of the compound, as revealed by the X-ray analysis, is similar to that of $H_3(\eta 5-C_5H_5)CoOs_3)(CO)_9$ described in Example 4 above; the compound comprises a tetrahedron of metal atoms with the toluene ligand being coordinated with the rhodium atom, three carbonyls being coordinated with each of the osmium atoms, and each of the Os—Os edges of the tetrahedron being abridged by a single hydrogrn atom. (The bridging hydrogen atoms were located directly from difference-Fourier synthesis and were well behaved during least-squares refinement.) The $C_{2h}^3$ symmetry of the crystal structure dictates that the molecule have $C_s(m)$ symmetry, which is achieved by the intrinsic 3-fold symmetry of the $(\mu-H)_3Os_3\text{-}CO)_9$ moiety, together with a 3-fold disorder of the methyl group on the toluene ligand, leading to the entire observed molecule having approximate $C_{3v}$ symmetry. Thus the proton NMR singlet at $\delta=2.33$ ppm. can be attributed to the methyl protons.

Further experiments showed that the yields of $H_3(\eta^6-C_6H_5CH_3)RhOs_3(CO)_9$ and $H_2(\eta^5-C_5H_5)RhOs_3(CO)_{10}$ based upon the $H_2Os_3(CO)_{10}$ starting material were not significantly affected by reducing the quantity of $(Rh(\eta^5-C_5H_5)(CO)_2$ used in the reaction to 2 moles per mole of $H_2Os_3(CO)_{10}$. All three of the products of this reaction were stable to air.

EXAMPLE 6

Preparation of $H_2(\eta^5-C_5H_5)RhOs_3(CO)_{10}$ and $H_3(\eta^6-C_6H_6)RhOs_3(CO)_9$ from $Rh(\eta^5-C_5H_5)(CO)_2$ 150 mg. of $H_2Os_3(CO)_{10}$ (0.176 mmol.) and 78 mg. of $(Rh(\eta^5-C_5H_5)(CO)_2)$ (0.35 mmol.) were reacted together under the same conditions as in Example 5 above except that the toluene solvent was replaced with the same quantity of freshly distilled and degassed benzene. Purification of the products was effected by chromatography in the same manner as in Example 5 above. The products were the same $H_2\eta^5-C_5H_5)RhOs_3(CO)_{10}$ and the unidentified brown solid described in Example 5 above, together with an orange-red compound, identified as $H_3(\eta^6-C_6H_6)RhOs_3(CO)_9$, the yield of this last compound being 10% based upon the $H_2Os_3(CO)_{10}$. The infrared spectrum of this last compound showed bands at 2070(w), 2048(s), 1994(vs), 1978(m) and 1945(vw) cm.$^{-1}$, suggesting a structure very similar to that of the corresponding compound have a toluene ligand described in Example 5 above. The proton nuclear magnetic resonance spectrum in hexadeuteroacetone at $-60°$ C. showed a singlet (6H) at $\delta=6.68$ ppm and a singlet (3H) at $\delta=-17.3$ ppm. The $^{13}C$ nuclear magnetic resonance spectrum of the compound in methylene chloride at the same temperature showed a singlet (3C) at $\delta=176.9$ ppm. and a doublet (6C, J=9 Hz.) at $\delta=172.1$ ppm. Both these nuclear magnetic resonance spectra are consistent with the structure just suggested; the singlet is attributable to the three axial carbonyls and the doublet to the six equatorial carbonyls (the benzene used was not enriched with $^{13}C$ so the benzene carbons were not observable).

EXAMPLE 7

Preparation of $H_2(\eta^5-C_5H_5)RhOs_3(CO)_{10}$ from $Rh(\eta^5-C_5H_5)(CO)_2$ The reaction and purification procedure of Example 6 above was repeated except that an equal volume of freshly distilled and degassed heptane was substituted for the benzene used in Example 6. The only identifiable product was $H_2(\eta^5-C_5H_5)RhOs_3(CO)_{10}$.

EXAMPLE 8

Preparation of $H_4(\eta^5-C_5(CH_3)_5)RhOs_3(CO)_9$ from $Rh(\eta^5-C_5(CH_3)_5)(CO)_2$.

150 mg. of $H_2Os_3(CO)_{10}$ (0.176 mmol.) and 103 mg. of $Rh(\eta^5-C_5(CH_3)_5)(CO)_2$ (0.35 mmol.) were placed in a 50 mol. three-necked flask equipped with a condensor and maintained under a nitrogen atmosphere. Approximately 20 ml. of freshly distilled and degassed heptane was added to the flask. Pre-purified hydrogen gas was slowly bubbled through the resultant reaction mixture which was heated to 90° C. and maintained at this temperature for 72 hours with stirring. The reaction mixture was then cooled to room temperature and the heptane removed under vacuum to leave and oil, which was redissolved in 5 ml. of methylene chloride and subjected to thin-layer chromatography under the same conditions as in Example 4 above. The only identifiable product was $H_4(\eta^5-C_5(CH_3)_5)RhOs_3(CO)_9$, obtained in a yield of 30 mg. (16% based on the $H_2Os_3(CO)_{10}$).

The infrared spectrum of this compound in hexane showed peaks at 2082(m), 2060(s), 2050(s), 2012(s), 1920(m), 1985(s), 1972(w,sh) and 1943(vw) cm.$^{-1}$. The proton nuclear magnetic resonance spectrum at $-60°$ C. showed an intense singlet (15H) at $\delta=1.94$ ppm, and incompletely resolved doublet (J = 18 Hz on a 300 MHz spectrum, 2H) and a singlet (2H) at $\delta=-19.68$ ppm. At 25° C., the 1.94 ppm. peak is unchanged, but the $-15.7$ ppm and $-19.68$ ppm peaks collapsed to a single peak at $\delta=-17.48$ ppm. These spectral data are consistant with a structure somewhat similar to that of $H_4(\eta^5-C_5H_5)CoOs_3(CO)_9$ described in Example 4 above but differing in the positions of the hydrogen atoms; the structure is based upon the usual tetrahedron of rhodium and osmium atoms with the pentamethylcyclopentadienyl ligand symmetrically coordinated to the rhodium atom and three carbonyls coordinated to each of the osmium atoms. However, only two of the Os—Os edges of the tetrahedron are bridged by hydrogen atoms, the remaining two hydrogen atoms bridging the two Rh—Os edges of the face of the tetrahedron which lacks a hydrogen bridge along its Os—Os edge. In the proton NMR spectrum, the 1.94 ppm resonance is attributable to the methyl protons, the $-15.17$ ppm doublet being attributable to the hydrogens bridging the Rh—Os edges (the resonances of these hydrogens will be split by the rhodium atom), and the $-19.68$ singlet to the hydrogens bridging the Os—Os edges. Evidently, the bridging hydrogens are mobile at room temperature.

EXAMPLE 9

The reaction and purification procedures of Example 8 above were repeated substituting an equal volume of toluene for the heptane solvent. The same product was obtained as in Example 8, except that the yield increased to 67.5 mg. (36% based upon the $H_2Os_3(CO)_{10}$). There was no trace of any compound produced by replacement of the pentamethylcyclopentadienyl ligand with a toluene ligand, as might be expected from the results described in Example 6 using the corresponding starting material with an unsubstituted cyclpentadienyl ligand.

The greenish-brown band produced 15 mg. (8% based on the $H_2Os_3(CO)_{10}$) of greenish-brown $H_2(\eta^5-C_5H_5)RhOs_3(CO)_{10}$. The infrared spectrum of this compound in cyclohexane showed peaks at 2083(m), 2063(vs), 2042(vs), 2010(vs), 2000(s,sh), 1982(m), 1970(m) and 1819(m) cm$^{-1}$.

EXAMPLE 10

Preparation of $H_4(\eta^5-C_5(CH_3)_5)RhOs_3(CO)_9$ and $H_2(\eta^5-C_5(CH_3)_5)_2 Rh_2Os_2(CO)_7$ from $Rh(\eta^5-C_5(CH_3)_5)(CO)_2$ 200 mg. of $H_2Os_3(CO)_{10}$ (0.23 mmol.) and 137 mg. of $Rh(\eta^5-C_5(CH_3)_5)(CO)_2$ (0.46 mmol.) were placed in a 100 ml. three-necked flash containing 50 ml. of toluene freshly distilled from calcium hydride. Pre-purified hydrogen gas was slowly bubbled through the resultant reaction mixture which was heated to 90°-100° C. and maintained at this temperature for 16 hours with stirring. After a spot check by thin-layer chromotography had indicated complete consumption of $H_2Os_3(CO)_{10}$, the reaction mixture was cooled to room temperature, evaporated almost to dryness and the resultant brown residue redissolved in the minimum amount (about 5 ml.) of methylene chloride and subjected to thin layer chromatography under the same conditions as in Example 4 above. Three bands were produced, these bands being orange, brown and green in descending $R_f$ value order. The green band was not characterized due to the small quantity of material produced. The orange band yielded 90 mg. (36.2% based on the $H_2Os_3(CO)_{10}$) of $H_4(\eta^5-C_5(CH_3)_5)RhOs_3(CO)_9$ indentical to the material obtained in Example 8 above.

The brown band yielded 94 mg. (38.9% based on the $H_2Os_3(CO)_{10}$) of a material having an infra-red spectrum (in hexane) displaying peaks at 2075(s), 2040(vs), 1996(m), 1987(s), 1955(m), 1948(m) and 1774(w) cm$^{-1}$. This compound was identified by its proton NMR specturm and a full X-ray structure determination as $H_2(\eta^5-C_5(CH_3)_5)_2Rh_2Os_2(CO)_7$; the space group is $P2_1/c$ ($C_{2h}^5$, #14) with a=10.923A, b=15.374A, c=17.869, $\beta=96.39°$, V=2981.67A$^3$, Z=4. The molecular weight of 1054.77 gives a calculated specific gravity of 2.349.

The structure of the compound, as revealed by the X-ray analysis, is based upon a distorted tetrahedron containing two osmium and two rhodium atoms. Each osmium carriers three carbonyls while each rhodium carries a pentamethylcyclopentadienyl ligand. The Os—Os edge and one Os—Rh edge are each bridged by a single hydride while the Rh—Rh is asymetrically bridged by a carbon; the two Rh—C distances for this bridging carbonyl are 1.950A and 2.019A while the two Rh-C-O angles differ by 75°.

It will be apparent to those skilled in the art that numerous modifications and variations can be made in the preferred processes of the invention described above. Accordingly, the foregoing description is to be construed in an illustrative and not a limitative sense, the scope of the invention being defined solely by the appended claims.

We claim:

1. $H(\eta^5-C_5H_5)MoOs_3(CO)_{14}$.
2. $H_3(\eta^5-C_5H_5)CoOs_3(CO)_9$.
3. $H_4(\eta^5-C_5H_5)CoOs_3(CO)_9$.
4. $H_2(\eta^5-C_5H_5)RhOs_3(CO)_{10}$.
5. $H_4(\eta^5-C_5(CH_3)_5)RhOs_3(CO)_9$.
6. $H_2(\eta^5-C_5(CH_3)_5)Rh_2Os_2(CO)_7$.
7. A process for producing $H_4(\eta^5-C_5(CH_3)_5)RhOs_3(CO)_9$ and $H_2(\eta^5-C_5(CH_3)_5))Rh_2Os_2(CO)_7$, which comprises establishing, in the presence of gaseous hydrogen, a reaction mixture comprising $Rh(\eta^5-C_5(CH_3)_5)(CO)_2$, $H_2Os_3(CO)_{10}$ and a solvent which at least partially solubilizes one of said $Rh(\eta^5-C_5(CH_3)_5)(CO)_2$ and said $H_2Os_3(CO)_{10}$, said reaction mixture being established in the substantial absence of molecular oxygen and water, thereby forming $H_4(\eta^5-C_5(CH_3)_5)RhOs_3(CO)_9$ and $H_2(\eta^5-C_5(CH_3)_5)Rh_2Os_2(CO)_7$ in said reaction mixture and recovering said $H_4(\eta^5-C_5(CH_3)_5)RhOs_3(CO)_9$ and $H_2(\eta^5-C_5(CH_3)_5)Rh_2Os_2(CO)_7$ from said reaction mixture.

8. A process according to claim 7 wherein said solvent solubilizes both said $Rh(\eta^5-C_5(CH_3)_5)(CO)_2$ and said $H_2Os_3(CO)_{10}$.

9. A process according to claim 8 wherein said solvent is an aliphatic or aromatic hydrocarbon solvent.

10. A process according to claim 9 wherein said solvent is heptane benzene or toluene.

11. A process according to claim 7 wherein the molar ratio of said $Rh(\eta^5-C_5(CH_3)_5)(CO)_2$ to said $H_2Os_3(CO)_{10}$ is at least about stoichiometric.

12. A process according to claim 11 wherein said reaction mixture comprises about two moles of said $Rh(\eta^5-C_5(CH_3)_5)(CO)_2$ per mole of said $H_2Os_3(CO)_{10}$.

13. A process according to claim 7 wherein said gaseous hydrogen is bubbled through said reaction mixture.

14. A process according to claim 7 which is conducted at a temperature in the range of about 80° to about 120° C.

15. A process according to claim 7 wherein said reaction mixture is chromatographed on silica gel using a hexane/benzene liquid phase to separate the products of said reaction.

16. A process according to claim 7 wherein said reaction mixture comprises said $Rh(\eta^5-C_5(CH_3)_5)(CO)_2$ and said $H_2Os_3(CO)_{10}$ in a molar ratio of at least about 1:1 and a non-polar solvent in which said $Rh(\eta^5-C_5(CH_3)_5)(CO)_2$ and said $H_2Os_3(CO)_{10}$ are soluble, said reaction mixture being established at a temperature in the range of about 80° to about 120° C. and said gaseous hydrogen being bubbled through said reaction mixture.

17. A rhodium tri-osmium carbonyl of the formula $H_3(\eta^6-\phi R_6)RhOs_3(CO)_9$ wherein $\phi R_6$ represents a benzene ring bearing six groups R each of said groups R being independently hydrogen or a methyl group.

18. The compound according to claim 17 wherein each group R represents a hydrogen, namely $H_3(\eta^6-C_6H_6)RhOs_3(CO)_9$.

19. The compound according to claim 17 wherein one group R represents a methyl group and the other five groups R represent hydrogen atoms, namely $H_3(\eta^6-C_6H_5CH_3)RhOs_3(CO)_9$.

20. A process for producing a rhodium tri-osmium carbonyl of the formula $H_3(\eta^6-\phi R_6)RhOs_3(CO)_9$, wherein $\phi R_6$ represents a benzene ring bearing six groups R, each of said groups R being independently hydrogen or a methyl group, said process comprising establishing, in the presence of gaseous hydrogen, a reaction mixture comprising $Rh(\eta^5-C_5H_5)(CO)_2$, $H_2Os_3(CO)_{10}$ and an aromatic solvent of the formula $\phi R_6$, said reaction mixture being established in the substantial absence of molecular oxygen and water, and recovering said $H_3(\eta^6-\phi R_6)RhOs_3(CO)_9$ from said reaction mixture.

21. A process according to claim 20 wherein said aromatic solvent is benzene or toluene.

22. A process according to claim 20 wherein the molar ratio of said $Rh(\eta^5-C_5H_5)(CO)_2$ to said $H_2Os_3(CO)_{10}$ is at least about stoichiometric.

23. A process according to claim 22 wherein said reaction mixture comprises about 2 moles of said $Rh(\eta^5-C_5H_5)(CO)_2$ per mole of said $H_2Os_3(CO)_{10}$.

24. A process according to claim 20 wherein said gaseous hydrogen is bubbled through said reaction mixture.

25. A process according to claim 20 which is conducted at a temperature in the range of about 80° to about 120° C.

26. A process according to claim 20 wherein said reaction mixture is chromatographed on silica gel using a hexane/benzene liquid phase to separate the products of said reaction.

27. A process according to claim 20 wherein said reaction mixture comprises said $Rh(\eta^5-C_5H_5)(CO)_2$ and said $H_2Os_3(CO)_{10}$ in a molar ratio of at least about 1:1, said reaction mixture being established at a temperature in the range of about 80° to about 120° C. and said gaseous hydrogen being bubbled through said reaction mixture.

* * * * *